United States Patent
Xue et al.

(10) Patent No.: US 7,183,314 B1
(45) Date of Patent: Feb. 27, 2007

(54) COMPOUND FOR TREATMENT OF ANXIETY AND METHODS OF PREPARATION AND USE THEREOF

(75) Inventors: Hong Xue, Hong Kong (HK); Hui Kwok Min, Hong Kong (HK); Hongyan Wang, Liaoning (CN); Hui Zheng, Beijing (CN)

(73) Assignee: Naturon Limited, Hong Kong (HK)

( * ) Notice: Subject to any disclaimer, the term of this patent is extended or adjusted under 35 U.S.C. 154(b) by 744 days.

(21) Appl. No.: 09/909,862

(22) Filed: Jul. 20, 2001

Related U.S. Application Data

(60) Provisional application No. 60/219,819, filed on Jul. 21, 2000.

(51) Int. Cl.
 *A61K 31/35* (2006.01)
 *A61K 31/335* (2006.01)

(52) U.S. Cl. .................. 514/456; 514/451; 514/452

(58) Field of Classification Search ............... 514/456, 514/451, 452
See application file for complete search history.

(56) References Cited

U.S. PATENT DOCUMENTS

| | | | |
|---|---|---|---|
| 5,707,630 A | 1/1998 | Morrow | 424/195.1 |
| 5,756,538 A | 5/1998 | Cassels et al. | 514/456 |
| 5,977,120 A | 11/1999 | Giles, Jr. | 514/264 |
| 6,004,998 A | 12/1999 | Cassels et al. | 514/456 |
| 6,080,410 A | 6/2000 | Bewicke | 424/195.1 |
| 6,080,780 A | 6/2000 | Paladini et al. | 514/456 |

OTHER PUBLICATIONS

Brzozowski T., et al., "SU-840, a Novel Synthetic Flavonoid Derivative of Sophoradin, with Potent Gastroprotective and Ulcer Healing Activity," J. Physiology & Pharm. 49(1) :83-98 (1998).

Dekermendjian, Kim et al., "Structure-Activity Relationships and Molecular Analysis of flavonoids Binding to the Benzodiazepine Site of the Rat Brain GABAA Receptor Complex," *J. Medicinal Chem.* 42(21):4343-4350 (1999).

Karton, Yishai et al., "Synthesis and Biological Activities of Flavonoid Derivatives as $A_3$ Adenosine Receptor Antagonists," *J. Med. Chem.*39:2293-2301 (1996).

Viola, H. et al., "6,3'-Dibromoflavone and 6-nitro-3'-bromoflavone; New Additions to the 6,3'-disubstituted Flavone Family of High-affinity Ligands of the Brain Benzo-diazepine Binding Site With Agonistic Properties," *Biochem. & Biophysical Res. Comm.* 273(2):694-698 (2000).

Wolfman, Claudia et al., "Pharmacological Characterization of 6-bromo-3'-nitroflavone, a Synthetic Flavonoid With High Affinity for the Benzodiazepine Receptors," *Pharm., Biochem. & Behavior*61(3):239-246 (1998).

Lim, S. S. et al., "Synthesis of Flavonoids and Their Effects on Aldose Reductase and Sorbitol Accumulation in Streptozotocin-induced Diabetic Rat Tissues," J. Pharmacy & Pharmacology 53(5):653-668 (2001).

(Continued)

*Primary Examiner*—Shengjun Wang
(74) *Attorney, Agent, or Firm*—Hamilton, Brook, Smith & Reynolds, P.C.

(57) ABSTRACT

A method for preventing or for treating anxiety in a patient in need thereof comprising administering wogonin to the patient in an effective dose that does not cause sedative or myorelaxant side effects. Methods for extracting wogonin from the roots of *Scutelleria baicalensis* Georgi are also described.

8 Claims, 3 Drawing Sheets

OTHER PUBLICATIONS

Woods, J.H., et al., "Benzodiazepines: Use, Abuse, and Consequences", *Pharmacological Reviews*, 44(2):151-347 (1992).

Barnard, D. L. et al., "Antiherpesvirus Activity and Mode of Action of SP-303, a Novel Plant Flavonoid," *Chemotherapy* 39:203-211 (1993).

Bonetti, E.P., et al., "Benzodiazepine Antagonist Ro 15-1788: Neurological and Behavioral Effects," *Psychopharmacology* 78:8-18 (1982).

Cushman, Mark et al., "Synthesis and Protein-Tyrosine Kinase Inhibitory Activities of Flavonoid Analogues," *J. Med. Chem.* 34:798-806 (1991).

Federici, Elena et al., "Antiplasmodial Activity of the Alkaloids of *Peschiera fuchsiaefolia*," *Planta Medica* 66:93-95 (2000).

Ferriola, Patrice C. et al., "Protein Kinase C Inhibition by Plant Flavonoids," *Biochem. Pharmacol.* 38(10):1617-1624 (1989).

File, Sandra E. and Pellow, Sharon, "The effects of triazolobenzodiazepines in two animal tests of anxiety and in the holeboard," *Br. J. Pharmac.* 86:729-735 (1985).

File, Sandra E. and Pellow, Sharon, "Intrinsic actions of the benzodiazepine receptor antagonist Ro 15-1788," *Psychopharmacology* 88:1-11 (1986).

File, Sandra E. and Wardill, Ann G., "Validity of Head-Dipping as a Measure of Exploration in a Modified Hole-Board," *Psychopharmacologia(Berl.)* 44:53-59 (1975).

Hu, Hong-Zhen and Li, Zhi-Wang, "Modulation by adenosine of GABA-activated current in rat dorsal root ganglion neurons," *J. Physiology* 501.1:67-75 (1997).

Hu, H.-Z et al., "Evidence for the Existence of Substance P Autoreceptor in the Membrane of Rat Dorsal Root Ganglion Neurons," *Neuroscience* 77(2):535-541 (1997).

Hui, Kwok Min et al., "Interaction of Flavones from the Roots of *Scutellaria baicalensis* with the Benzodiazepine Site," *Planta Medica* 66:91-93 (2000).

Kimuya, Yoshiyuki et al.., "Studies on *Scutellariae* Radix. IV. Effects on Lipid Peroxidation in Rat Liver," *Chem. Pharm. Bull.* 29(9):2610-2617 (1981).

Kubo, Michinori et al., "Studies on *Scutellariae* Radix," *Planta medica* 43:194-201 (1981).

Lin, Chun-Ching and Sheih, Den-En, "The Anti-inflammatory Activity of *Scutellaria rivularis* Extracts and Its Active Components, Baicalin, Baicalein and Wogonin," *American J. Chinese Med.* 24(1):31-36 (1996).

Lister, Richard G., "The use of a plus-maze to measure anxiety in the mouse," *Psychopharmacology* 92(2):180-185 (1987).

Medina, Jorge H. et al., "Chrysin (5,7-DI-OH-Flavone), A Naturally-Occurring Ligand for Benzodiazepine Receptors, with Anticonvulsant Properties," *Biochem. Pharmacol.* 40(10):2227-2231 (1990).

Miksicek, Richard J., "Commonly Occurring Plant Flavonoids Have Estrogenic Activity," *Molecular Pharmacology* 44:37-43 (1993).

Nolan, Norma A. and Parkes, M.W., "The Effects of Benzodiazepines on the Behaviour of Mice on a Hole-Board," *Psychopharmacol.* 29:277-288 (1973).

Oyama, Yasuo et al., "Myricetin and quercetin, the flavonoid constituents of *Ginkgo biloba* extract, greatly reduce oxidative metabolism in both resting and $Ca^{2+}$—loaded brain neurons," *Brain Research* 635:125-129 (1994).

Paladini, A.C. et al., "Flavonoids and the Central Nervous System: from Forgotten Factors to Potent Anxiolytic Compounds," *J. Pharm. Pharmacol.* 51(5):519-526 (1998).

Pellow, Sharon et al., "Validation of open:closed arm entries in an elevated plus-maze as a measure of anxiety in the rat," *J. Neuroscience Methods* 141:149-167 (1985).

Salgueiro, J.B., et al., "Anxiolytic Natural and Synthetic Flavonoid Ligands of the Central Benzodiazepine Receptor Have No Effect on Memory Tasks in Rats," *Pharmacol. Biochem.& Behavior* 58(4):887-891 (1997).

Sigel, Erwin et al., "The Effect of Subunit Composition of rat Brain $GABA_A$ Receptors on Channel Function," *Neuron* 5:703-711 (1990).

Sigel, E., "Effects of veratridine on single neuronal sodium channels expressed in *Xenopus* oocytes," *Pflugers Archiv —European J. Physiology* 410:112-120 (1987).

Wolfman, Claudia et al., "Possible Anxiolytic Effects of Chrysin, a Central Benzodiazepine Receptor Ligand Isolated from *Passiflora coerulea,*" *Pharmacology Biochem& Behavior* 47:1-4 (1994).

Harborne, J.B. Editor, "*The Flavonoids*" London, Chapman & Hall, publisher:406-463 (1994).

COMPOUND FOR TREATMENT OF ANXIETY AND METHODS OF PREPARATION AND USE THEREOF

RELATED APPLICATION

This application claims the benefit of U.S. Provisional Application No. 60/219,819, filed on Jul. 21, 2000. The entire teachings of the above application are incorporated herein by reference.

BACKGROUND OF THE INVENTION

Benzodiazepines (BZDs) are extremely effective anxiolytics, and are among the most widely prescribed psychoactive drugs in current therapeutic use. BZDs, however, also exhibit undesirable side effects including sedative and myorelaxant activity.

*Scutellaria baicalensis* Georgi (commonly known as Huang Qin in Chinese and Ougon in Japanese) is one of the most important medicinal herbs in traditional Chinese medicine. It possesses anti-bacterial activity, sedative effects and finds application in the treatment of a range of conditions including diarrhea (Kubo, M., et al, *Planta Medica* 43:194–201, 1981) and hepatitis (Kimuya, Y., et al., *Chem Pharm Bull* 29: 2610–2617, 1981). Several individual compounds, including wogonin, baicalin, baicalein, scutellarein and skullcapflavone, have been extracted from this medicinal herb and tested for affinity to the benzodiazepine site (BZD-S) of the $GABA_A$ receptor to identify strongly binding ligands suitable for further study. The reports regarding the binding capacity of *Scutellaria baicalensis* Georgi extracts have been contradictory (Hui, K M, et al., *Planta Med* 56 91–93, 2000).

SUMMARY OF THE INVENTION

This invention is based, at least in part, on the unexpected discovery that the compound of the formula:

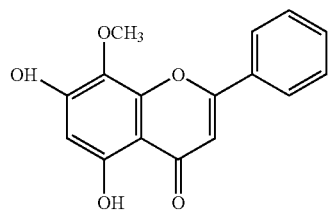

(commonly known and referred to herein as wogonin) provides extremely effective anxiolytic treatment without significant sedative or myorelaxant side effects. The degree of efficacy demonstrated when this compound is administered in vivo is surprising because while binding affinity of the wogonin to the BZD-S of the $GABA_A$-receptor has been variously reported as weak or moderate, it has not been rated as a strong ligand for that receptor. Therefore, the very positive results obtained in the studies, performed using the models accepted in the art as demonstrating efficacy for anxiolytic treatment, were unexpected. Utilizing wogonin as a medicament for the treatment of anxiety provides a number of advantages. The compound is naturally occurring, being a component contained in the roots of the *Scutellaria baicalensis* Georgi herb, and is known to have a very low toxicity. Moreover, the compound is abundant in the herb, making its extraction both efficient and economical. Methods for efficiently extracting the compound in good yield and high purity are also provided.

In one embodiment, the invention is directed to a method of preparing a compound of the formula:

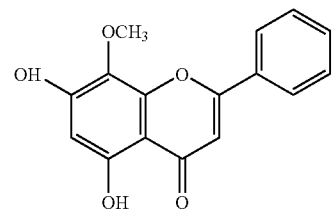

including extracting the compound from the roots of *Scutellaria baicalensis* Georgi using a solvent, filtering the extract, concentrating the extract, and forming crystals of the compound from the concentrated extract. In a particular embodiment, the roots of *Scutellaria baicalensis* Georgi are in the form of a powder. The solvent can be dichloromethane or ethanol. The steps of the method can be performed at standard temperature and pressure. The crystals formed from the concentrated extract can have a purity of from about 85% to about 99%, and the product yield can be from about 0.2% to about 0.8%.

In another embodiment, the invention is directed to the product obtainable by the method of preparation described above. The product can be contained in a pharmaceutically acceptable formulation.

In another embodiment, the invention is directed to the use of wogonin for the manufacture of a medicament for treating anxiety. In a particular embodiment, wogonin is used for the manufacture of a medicament for treating anxiety without sedative and/or myorelaxant effects.

In another embodiment, the invention is directed to the use of a medicament for treatment of anxiety consisting essentially of a compound of the formula as shown above.

In yet another embodiment, the invention is directed to a method of treating anxiety in a patient comprising administering an effective non-toxic dose to the patient of a compound of the formula shown above, wherein the medicament provides anxiolytic treatment without sedative and myorelaxant side effects.

In a particular embodiment, the dose administered to the patient is from about 0.15 mg/kg to about 1.0 mg/kg. The dose can be administered in a single aliquot, or alternatively the dose can be administered in more than one aliquot.

In another aspect, the invention is directed to a pharmaceutical package comprising one or more containers filled with the compound. The package can further contain instructions for using the compound in the treatment of anxiety.

In yet another embodiment, the invention is directed to a method of treating anxiety in a patient comprising administering an effective non-toxic dose of wogonin to the patient.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
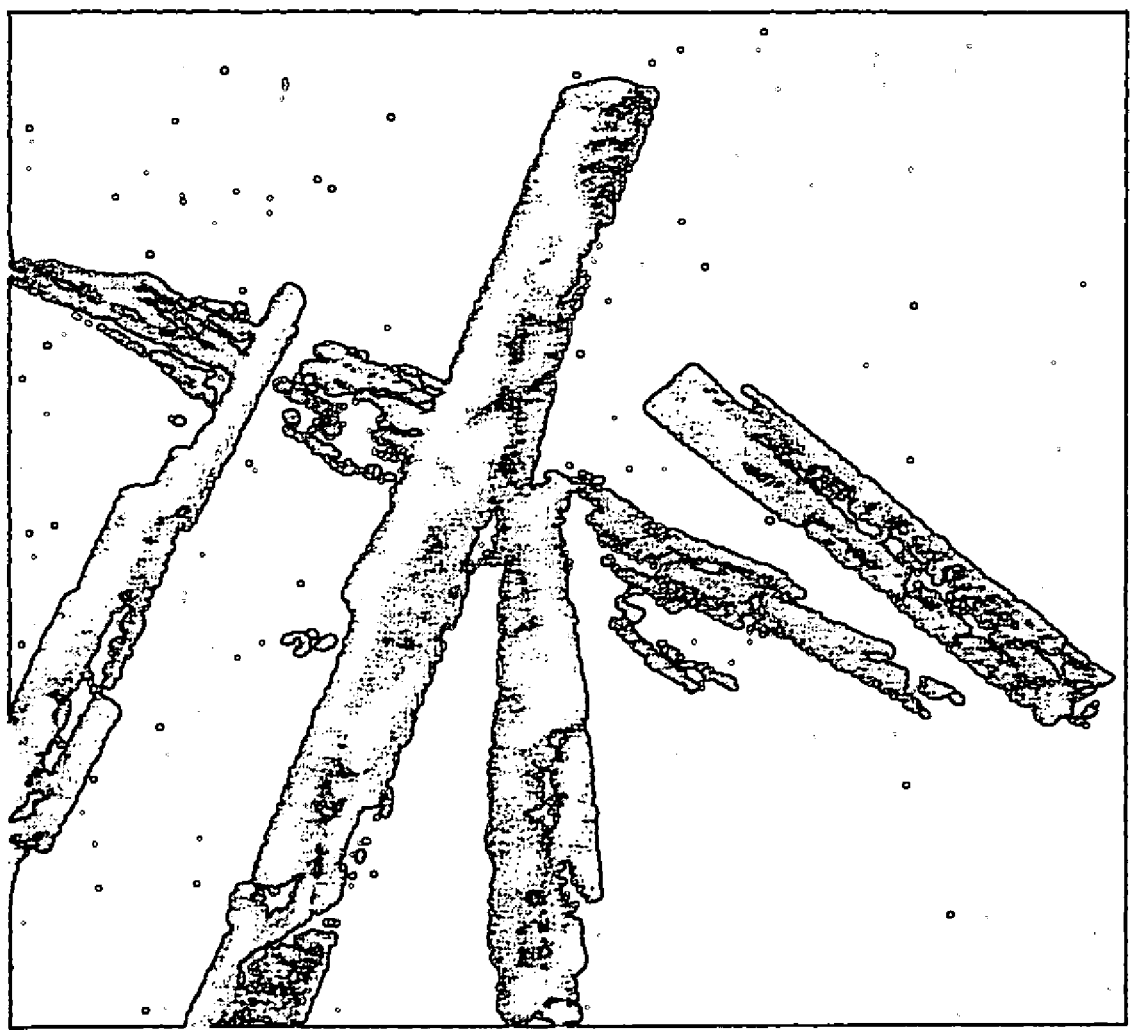
FIG. 1 is a micrograph of wogonin showing its needle shaped crystals.

A description of preferred embodiments of the invention follows.

This invention is based, at least in part, on the unexpected discovery that the compound of the formula:

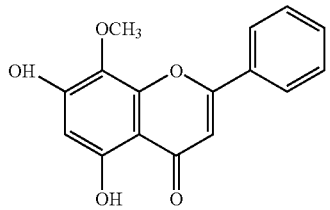

(commonly known and referred to herein as wogonin) provides extremely effective anxiolytic treatment without significant sedative or myorelaxant side effects. The degree of efficacy demonstrated when this compound is administered in vivo is surprising because while binding affinity of the wogonin to the BZD-S of the $GABA_A$-receptor has been variously reported as weak or moderate, it has not been rated as a strong ligand for that receptor. Therefore, the very positive results obtained in the studies, performed using the models accepted in the art as demonstrating efficacy for anxiolytic treatment, were unexpected. Utilizing wogonin as a medicament for the treatment of anxiety provides a number of advantages. The compound is naturally occurring, being a component contained in the roots of the *Scutellaria baicalensis* Georgi herb, and is known to have a very low toxicity. Moreover, the compound is abundant in the herb, making its extraction both efficient and economical.

Methods for efficiently extracting the compound in good yield and high purity are provided. The methods include extracting wogonin from the roots of the *Scutellaria baicalensis* Georgi herb where it is contained in large quantity. Other portions of the *Scutellaria baicalensis* Georgi herb can also be utilized in the process, as can other herbs which are known to contain wogonin. Table 1 provides a non-limiting list of herbs known to contain wogonin.

TABLE 1

Plants of the genus *Scutellaria*

*Scutellaria baicalensis* Georgi
*S. amonea* C. H. Wright
*S. barbata* D. Don (*S. rivularis* Wall)
*S. hypericifolia* Levl.
*S. indica* L.
*S. likiangensis* Diels TABLE 1-continued

*S. planipes*
*S. rehderiana* Diels
*S. strigillosa* Hemsl.
*S. tenax* W. W. Smith var. *patentipilosa*
*S. viscidula* Bunge
Plants of other Genera

*Sorbaria sorbifolia*
*Tetracera indica*

The herb can be formed into a fine powder by crushing, grinding or other methods prior to the extraction of wogonin. The extraction process can utilize a chlorinated solvent such as dichloromethane or an alcohol such as methanol, ethanol or n-butanol. Ethyl ether, acetone and ethyl acetate as well as other solvents known in the art are also suitable for use in the methods of the invention. Any number of extractions can be performed including 1, 2, 3, 4, 5, 6 or more extractions. The extraction can be performed at standard temperature and pressure, e.g., 25° C. and 1 atmosphere. The extraction can also be performed at other temperatures and pressures. In a particular embodiment, the extraction is performed at the boiling point of the solvent used in the extraction.

The extract can be filtered by any suitable method, including filtering with standard filter paper. The extract can also be concentrated by any suitable method, including concentration achieved through the use of an evaporator.

Crystals of the compound can be formed by dissolving the extract in a solvent, such as ethanol, and allowing it to remain at room temperature for a suitable period of time. The crystals formed can be filtered and washed with a suitable solvent, such as ethanol.

Other methods are also exemplified.

The methods described produce a product with high purity in good yield. The product produced generally has a purity range of from about 85% to about 99%, with an average purity of about 95%. Estimated yield of extraction is about 0.2–0.8%, meaning 0.2–0.8 g of wogonin are produced per 100 g of *Scutellaria baicalensis* root. The product is also non-toxic even at very high levels, having an LD50 in mice of about 4 g/kg.

The wogonin product produced is very useful in the treatment of anxiety. Not only is it effective in diminishing the symptoms associated with anxiety, but as evidenced by the exemplification which follows, it does so without producing undesirable sedative or myorelaxant effects, even when administered at high doses. In general, wogonin is administered to a patient suffering from anxiety in an effective non-toxic dose. Although wogonin may be administered by a variety of methods, including oral, rectal, nasal, vaginal and parenteral, oral delivery is generally preferred.

The phrase "an effective non-toxic dose" as used herein means that amount of the compound, or the pharmaceutical composition comprising the compound which is effective for the compound to provide its intended function, e.g., to provide anxiolytic treatment, while not causing toxic side effects. The effective non-toxic dose can vary depending on such factors as the size of the patient and the severity of the anxiolytic state. One of ordinary skill in the art can study the aforementioned factors and make a determination regarding an effective non-toxic dose without undue experimentation. In particular embodiments, wogonin is administered in a range of from about 0.6 mg/kg to about 1.0 mg/kg, preferably from about 0.1 mg/kg to about 0.7 mg/kg, most preferably from about 0.15 mg/kg to about 10.35 mg/kg. Administration may be in a single aliquot or 2, 3, 4, 5 or more aliquots.

Wogonin is useful in treating both acute episodes of anxiety and chronic anxiety states. Its nontoxic properties make it particularly suitable for administration both when large doses are required, and when smaller doses extend over long periods of time. For example, wogonin can be administered in a single large dose to treat a patient experiencing a "panic attack", a type of crisis state associated with some types of anxiety. Wogonin can also be administered in smaller doses provided over a period of time to control anxiety. In a particular embodiment, wogonin can be administered prior to surgery to alleviate anxiety and to induce a state of relaxation in the patient. Such treatment not only diminishes the pre-surgical stress experienced by the patient, but can minimize the amount of general anesthesia which must be administered during the surgical procedure.

Wogonin can be administered in the form produced in the methods of the invention, or it can be admixed with various pharmaceutically or physiologically acceptable components. The phrase "pharmaceutically or physiologically acceptable" as used herein refers to those compounds, compositions containing such compounds, and/or dosage forms which are, within the scope of sound medical judgments, suitable for use.

The wogonin compound of the present invention can exist in free form or, where appropriate, in salt form. Pharmaceutically or physiologically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids or bases.

The invention also relates to pharmaceutical compositions comprising a therapeutically effective amount of wogonin and a pharmaceutical carrier or excipient. Carriers include, e.g., saline, buffered saline, dextrose, water, glycerol, ethanol, and combinations thereof. The composition, if desired, can also contain minor amounts of wetting or emulsifying agents, or pH buffering agents. The composition can be a liquid solution, suspension, emulsion, tablet, pill, capsule, sustained release formulation or powder. The composition can be formulated as a suppository, with conventional binders and carriers such as triglycerides. Oral formulations can include standard carriers such as pharmaceutical grades of mannitol, lactose, starch, magnesium stearate, sodium saccharine, cellulose, magnesium carbonate and others known to those of skill in the art. The pharmaceutical carrier may be either a solid or a liquid.

Illustrative solid carriers include lactose, terra alba, sucrose, talc, gelatin, agar, pectin, acacia, magnesium stearate, stearic acid, and the like. A solid carrier can include one or more substances which may also act as flavoring agents, lubricants, solubilizers, suspending agents, filler, glidants, compression aids, binders or tablet disintegrating agents; it can also be an encapsulating material. In powders, the carrier is a finely divided solid which is in admixture with the finely divided active ingredient. In tablets, the compound is mixed with a carrier having the necessary compression properties in suitable proportions, and compacted in the shape and size desired.

Illustrative liquid carriers include syrup, peanut oil, olive oil, water and the like. Liquid carriers are used in preparing solutions, suspensions, emulsions, syrups and elixirs. The composition can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweetners, flavoring agents, suspending agents, thickening agents, colors, viscosity regulators and stabilizers.

A wide variety of pharmaceutical forms can be employed. If a solid carrier is used, the preparation can be tableted, placed in a hard gelatin capsule in powder or pellet form or in the form of a troche or lozenge. If a liquid carrier is use, the preparation will be in the form of a syrup, emulsion or soft gelatin capsule.

Wogonin can be conveniently supplied in standard pharmaceutical packaging. Such containers are well known in the art. Instructions for the proper use of wogonin as a medicament or for the particular use of wogonin as a medicament in the treatment of anxiety can be supplied with the packaging.

EXAMPLES

Extraction And Purification of Wogonin

Large-scale preparation of wogonin can be achieved conveniently by using the following methods:

Crystallization Method

The roots of *Scutellaria baicalensis* Georgi were ground into powder and 500 g of the resulting powder were extracted three times, each time with 2 L of dichloromethane, at room temperature. The extract was filtered with Whatman No. 1 filter paper and concentrated to 200 ml in a rotary vacuum evaporator at 60° C. The yellow precipitate (DCM extract) at the bottom was filtered with Whatman No. 1 filter and dried. The yellow precipitate (1.5 g) was dissolved in 40 ml ethanol under reflux. This solution was filtered and kept at room temperature for crystal formation. The wogonin crystals which have the appearance of yellow needle shaped crystals were filtered and washed with ethanol (see FIG. 1).

After crystallization, the purity of wogonin was first checked by TLC (mobile phase, DCM: methanol, 10:1), and then further determined by HPLC using a Vydac $C_{18}$ reverse phase column (150×3.9 mm). The mobile phase used was acetonitrile and water (3:7) and it eluted at a flow rate of 1:0 ml/min. The injection volume was 100 μl, while detection wavelength was set at 280 nm. The HPLC system utilized includes a Waters 7120 WISP injector, a DU-65 spectrophotometer, a Waters 600E system controller and a Waters 486 tunable absorbance detector.

On the TLC plate, there was only a single spot observed from the woginin preparation. Based on the HPLC profile, the purity of the preparation was estimated at about 95% of wogonin.

Percolation Method

The pulverized sample (100 g) was percolated overnight with methanol or dichloromethane. The crude extracts were obtained by reduced pressure evaporation and then subjected to column chromatography over silica gel and eluted with chloroform-methanol.

Reflux Method

The pulverized sample (100 g) was refluxed three times with ethanol. The ethanol extracts were obtained after removal of the ethanol under reduced pressure evaporation. The extract was dissolved in water and shaken successively with ethyl ether and n-butanol. The ethyl ether layer was evaporated to dryness. The ethyl ether extract was subjected to column chromatography over silica gel and eluted with chloroform-methanol.

Ultrasonic Shaking Method

The pulverized sample (100 g) was extracted three times with 2000 ml of solvent by ultrasonic shaking for 30 minutes. Various extractions solvents were used: 70% methanol, methanol, ethanol, acetone and ethyl acetate. These extracts were subjected to column chromatography over silica gel and eluted with chloroform-methanol.

Supercritical Fluid Extraction (SFE) Method

The pulverized sample (100 g) was packed into a 1000 ml sample cartridge. Methanol or 70% methanol (100 ml, 200 ml and 300 ml, respectively was added), and 2000 ml liquid carbon dioxide was used as extraction solvent. The extraction temperature was set at 40, 50, 60 and 70° C., respectively. Liquid carbon dioxide at high pressure (200, 300 and 400 bar) was then allowed to flow into the sample cartridge. When the pressure reached 200, 300, and 400 bar, the vent valve of the extractor was opened immediately and carefully, so that the soluble fraction was collected through tubing to a test tube filled with 1000 ml methanol. The extraction process was run for 10~15 minutes, and was repeated three times. The crude extract was obtained by reduced pressure evaporation and then subjected to column chromatography over silica gel and eluted with chloroform-methanol.

TABLE 2

Yields of wogonin from *Scutellaria baicalensis* Georgi

| Extraction mode/Solvent | Yield (mg of Wogonin/g of dried root) |
| --- | --- |
| Percolation Overnight | |
| Methanol | 2.8 |
| Dichloromethane | 4.0 |
| Reflux | |
| Ethanol | 3.2 |
| Ultrasonic Shaking | |
| Methanol:Water (70:30) | 2.3 |
| Methanol | 2.8 |
| Ethanol | 2.7 |
| Supercritical Fluid Extraction | |
| Methanol:Water (70:30) | 2.2 |
| Methanol | 3.7 |

Electrophysiological Effects on Dorsal Root Ganglion Neurons

Freshly isolated neurons from adult rat dorsal root ganglion (DRG) of 2–3 weeks old Sprague-Dawley rats were prepared as described previously (Hu, et al., *Neurosci* 77: 535–541, 1997). The animal was decapitated and the vertebral column from thoracic to lumbar segments was dissected rapidly. DRGs were isolated and transferred to a petri dish containing Dulbecco's Modified Eagles' Medium (DMEM, Sigma) at pH 7.4, 349 mosmol/L immediately. After the removal of attached nerves and surrounding connective tissues, the DRGs were minced and then transfer red to a flask containing 5 ml of DMEM in which trypsin (0.5 mg/ml, type III, Sigma), collagenase (1 mg/ml, type 1A, Sigma) and Dnase (0.1 mg/ml, type IV, Sigma) had dissolved and incubated at 35° C. for 35 to 40 minutes in a shaking water bath. At the end of the incubation, soybean trypsin inhibitor (1.25 mg/ml, type II-S, Sigma) was added to stop digestion by trypsin. The isolated neurons (15–60 µm in diameter) were then placed into a 35 mm culture dish and kept still for at least 30 minutes before performing electrophysiological recording.

Whole-cell patch-clamp recordings were performed on the DRG neurons at room temperature (22–25° C.) using a CEZ-2400 patch/whole-cell amplifier (Nihon Kohden, Japan). Gigaohm seals were made using borosilicate glass microelectrodes with tip resistance of 2–4 MΩ. The membrane potential was usually held at −60 mV, unless noted otherwise. Neurons were placed in an extracellular medium containing (in mM): NaCl 150, KCl 5, $CaCl_2$ 2.5, $MgCl_2$ 2,4-(2-hydroxethyl)-1 piperazine-ethane sulfonic acid (HEPES) 10, D-glucose 10; pH was adjusted to 7.3 with NaOH, and osmolarity was adjusted to 340 mosmol/L with sucrose. The patch-pipettes were filled with an intracellular solution containing (in mM): CsCl 140, $MgCl_2$ 2.5, HEPES 10, ethylenebis (oxonitrilo) tetraacetate (EGTA) 11, Mg-ATP 5; pH was adjusted to 7.3 with CsOH and osmolarity was adjusted to 310 mosmol/L with sucrose. Membrane currents were filtered at 1 KHz(−3 dB), data were stored and analyzed on a laboratory computer with a data acquisition software and hardware system (Huazhoung University of Science and Technology, Wuhan China) or recorded by a pen recorder (Nihon Kohden).

Gamma amino butyric acid (GABA), wogonin and diazepam were dissolved in the extracellular solution, and applied to the neurons by gravity flow using a linear barrel array made of fused silica tubes (external diameter/internal diameter=500/200 µM) connected to a series of independent reservoirs. The tubes were placed within 100 µM of the neurons. Neurons were bathed constantly in extracellular medium flowing from one barrel and drug solutions were applied by opening the appropriate valve and rapidly shifting of the pipette array horizontally using a micromanipulator.

To allow full recovery of $GABA_A$ receptor from desensitization, drugs were applied at intervals of 4 minutes each.

Figure 2:
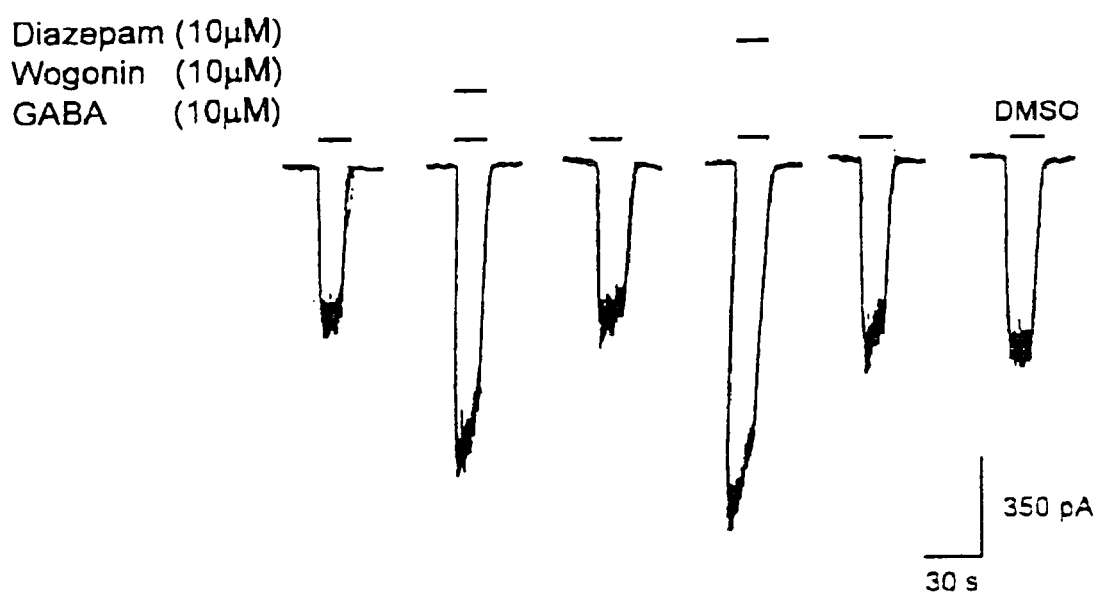
FIG. 2 shows a representative current trace (n=6) obtained from DRG neuron using the whole-cell patch clamp technique.

The electric current tracings showing the enhancement of GABA effects on the neurons by diazepam and by wogonin are shown in FIG. 2. The figure shows a representative current trace (n=6) obtained from DRG neuron using the whole-cell patch clamp technique. Wogonin enhanced the GABA-activated current in the same manner as diazepam (FIG. 2).

Pharmacological Tests

Male ICR mice weighing 18–23 g were used. They were housed in groups of four or five with free access to food and water and maintained on a 11 hour light: 13 hour dark cycle. All of the experimental groups, except acute lethal activity test (10 mice of either sex) have 16 animals per group.

Wogonin and diazepam were dissolved in water (pH10) and administrated orally 1 hour before testing in concentrations to give an injection volume of 10 ml/kg. For the chronic test, mice received 5 days pretreatment before the test. Flumazenil (Ro15-1788) was administrated intraperitoneally (IP) 15 minutes before testing in an injection volume of 12.5 ml/kg.

Locomotor Activity Test

A ZIL-2 apparatus (Beijing Institute of Materia Medica) with dimensions 60×60×12 cm was used. It consists of four circular plastic boxes with diameter 25 cm and each has 6 equally distributed infrared photocells. The locomotor activity was counted automatically during a 5 minute period of test. An increase in the number of transitions reflects an increased locomotor activity.

The results recorded in Table 3 show that up to 30 mg/kg body weight did not induce any sedative effects evidenced by no significant change in motor activity.

TABLE 3

| Drug (mg/kg) | Head-dip | | Locomotor |
| --- | --- | --- | --- |
| | Number | Time | Activity Score |
| Acute | | | |
| Vehicle | 23.13 ± 1.84 | 26.88 ± 2.01 | 201.81 ± 10.55 |
| 3.75 | 23.88 ± 1.08 | 27.00 ± 1.10 | 189.44 ± 6.54 |
| 7.5 | 31.06 ± 1.88* | 36.38 ± 1.93* | 205.63 ± 13.11 |
| 15 | 37.00 ± 1.94** | 42.25 ± 2.54** | 207.38 ± 10.12 |
| 30 | 42.75 ± 3.58** | 48.19 ± 3.92** | 193.50 ± 6.39 |
| diazepam 1 | 28.88 ± 2.16 | 37.00 ± 0.79* | 225.29 ± 15.80 |
| Chronic | | | |
| Vehicle | 22.44 ± 1.64 | 26.25 ± 1.71 | 178.50 ± 8.90 |
| 3.75 | 23.88 ± 1.86 | 26.88 ± 1.95 | 149.75 ± 6.55 |
| 7.5 | 32.31 ± 1.80** | 38.00 ± 0.79** | 170.56 ± 12.00 |
| 15 | 32.81 ± 2.27** | 37.38 ± 2.32** | 172.75 ± 6.25 |
| 30 | 30.13 ± 1.59* | 35.88 ± 1.81** | 184.56 ± 7.88 |
| Diazepam 1 | 31.94 ± 3.57* | 36.50 ± 3.59* | 195.25 ± 13.03 | n = 16 per group
*P < 0.05, **P < 0.01, significantly different from controls, Dunnett's t test after analysis of variance Holeboard Test The holeboard was a wooden box, 60×60×30 cm, with four holes of 3 cm diameter equally spaced in the floor. Mice were placed in the center of the holeboard and the number of head-dips, the time spent head-dipping were counted during 5 minutes (File, S. E., and Pellow, S., *Br J Pharmacol* 86: 729–735, 1985). Mice were allocated to different test groups randomly, and tested in an randomized order of drug treatment between 8 A.M. and 12 P.M. in a room lit by dim light. After each trial, the floor of the apparatus was wiped and dried thoroughly with tissue to remove traces of the previous path. An increase in the number and time spent head-dipping in this test are indicative of a greater exploratory activity. Conversely, a decrease in any of these parameters compared to controls is symptomatic of sedated behavior (Nolan, N. A., and Parkes, M. W., *Psychopharmacol* 29: 277–288, 1973; File, S. E., and Wardill, A. G., *Psychopharmacol* 44: 53–59, 1975; File, S. E., and Pellow, S., *Psychopharmacol* 88:1–11, 1986).

The results tabulated in Table 3 show that up to 30 mg/kg did not induce a significant sedative effect on the animals.

Elevated Plus-Maze

The elevated plus-maze was made of wood and consisted of two open arms (25×5 cm) and two opposite arms enclosed by 20 cm high walls. The arms extended from a central platform (5×5 cm). The plus-maze was elevated to a height of 40 cm. The maze was put inside a box 30×30×50 cm. After 5 minutes holeboard test, each mouse was immediately placed in the central square facing a closed arm and its behavior was observed for 5 minutes. The number of entries into and the time spent on the open and closed arms were counted. The total number of arm entries provided a measure of general activity, and anxiety reduces the number of such entries. At the end of the test, the number of entries into open arms was expressed as a percentage of the total number of arm entries. The time spent on the open arms was also expressed as a percentage of time spent on both the open and closed arms. Testing took place between 8 A.M. and 12 P.M. Mice were randomly allocated to different test groups, and tested in a randomized order of drug treatment in a room lit by dim light. After each trial, the floor of the apparatus was wiped and dried thoroughly with tissue to remove traces of the previous path. A selective increase in the parameters corresponding to open arms reveals an anxiolytic effect (Pellow, S., et al., *J Neurosci Meth* 14: 149–167, 1985; Lister, R. G., *Psychopharmacol* 92: 180–185, 1987).

Figure 3:
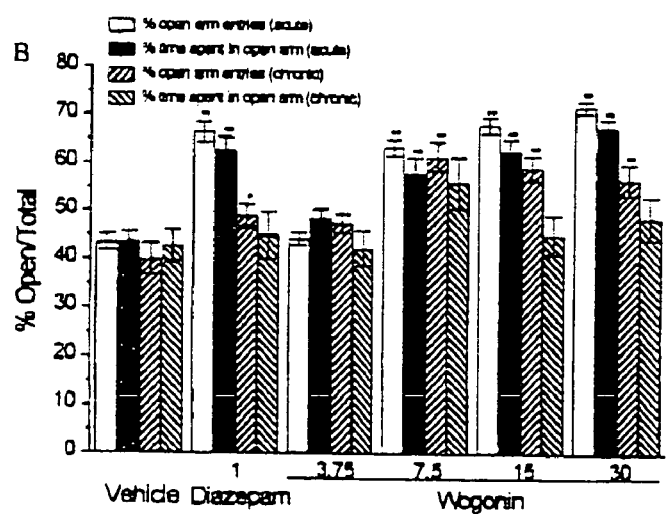
FIG. 3 shows the results of an elevated plus-maze test in mice given a 5 minute test, 1 hour after oral administration, acutely or chronically, with vehicle or test drugs.

The results summarized in Table 4 and FIG. 3 show that with respect to open arm entries (acute), % time spent in open arms (acute) and % open arm entries (chronic), wogonin displayed significant anxiolytic effects at 7.5, 15 or 30 mg/kg. FIG. 3 shows mean (±S.E.M.) total percentage of open arm entries or of time spent in the open arms of an elevated plus-maze in mice given a 5 minute test, 1 hour after oral administration acutely or chronically with vehicle or test drugs. *P<0.05, **P<0.01 are significantly different from control, Dunnett's t test after analysis of variance (n=16).

Figure 4:
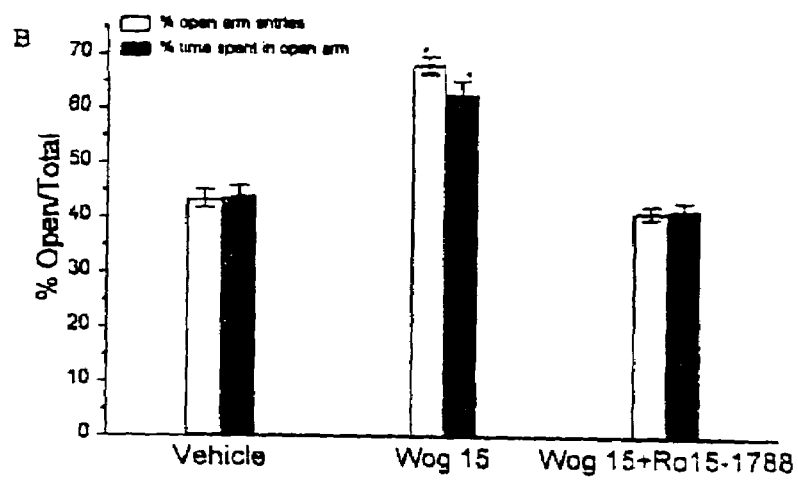
FIG. 4 shows the results of an elevated plus-maze test in mice given a 5 minute test, 1 hour after oral administration, acutely or chronically, with vehicle or test drugs.

Moreover, the anxiolytic effect of wogonin was completely abolished by the benzodiazepine receptor antagonist Flumazenil Ro15-1788. FIG. 4 shows the mean (±S.E.M.) total percentage of open arm entries or of time spent in the open arms of an elevated plus-maze in mice given a 5 minute test, 1 hour after oral administration acutely or chronically with vehicle or test drugs. The anxiolytic effect of wogonin was completely abolished by the treatment with Flumazenil Ro15-1788 (2.5 mg/kg). *P<0.01 is significantly different from control, Dunnett's t test after analysis of variance (n=16).

TABLE 4

| Drug (mg/kg) | Total |
| --- | --- |
| Acute | |
| Vehicle | 34.31 ± 1.78 |
| 3.75 | 34.56 ± 0.97 |
| 7.5 | 45.56 ± 1.71* |
| 15 | 43.50 ± 1.90* |
| 30 | 47.00 ± 1.93* |
| Diazepam 1 | 45.13 ± 2.31* |
| Chronic | |
| Vehicle | 25.94 ± 1.94 |
| 3.75 | 27.56 ± 1.90 |
| 7.5 | 31.75 ± 2.07 |
| 15 | 31.56 ± 2.13 |
| 30 | 31.31 ± 1.77 |
| Diazepam 1 | 29.38 ± 2.67 | n = 16 per group
*P < 0.01, Dunnett's t test after analysis of variance

Horizontal Wire Test

Mice were lifted by the tail and allowed to grasp a horizontally strung wire (1 mm diameter, 15 cm long and placed 20 cm above the table) with their forepaws and released (Bonetti, E. P., et al., *Psychopharmacol* 78: 8–18, 1982). The number of mice out of ten that did not grasp the wire with their forepaws or actively grasped the wire with at least one hind paw within 3 seconds was determined. After two trials performed at 5 minute intervals, the test took place. A myorelaxant drug impairs the capacity of the mice to grasp the wire. Such muscle relaxation is commonly associated with sedation.

Figure 5:
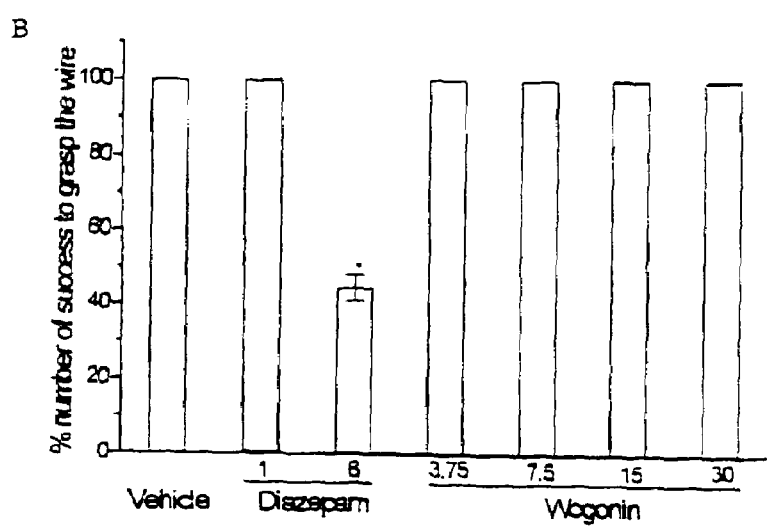
FIG. 5 shows the perfomance of mice in the horizontal wire test 1 hour after oral administration of vehicle or test drugs.

The results shown in FIG. 5 indicates that up to 30 mg/kg was devoid of myorelaxant effects.

While this invention has been particularly shown and described with references to preferred embodiments thereof, it will be understood by those skilled in the art that various changes in form and details may be made therein without departing from the scope of the invention encompassed by the appended claims. All references cited herein are hereby incorporated by reference.

What is claimed is:

1. A method of treating anxiety in a patient in need thereof comprising administering an effective non-toxic dose to the patient of a compound of the formula:

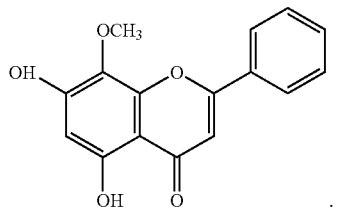

2. The method of claim 1, wherein the dose administered to the patient is from about 0.15 mg/kg to about 1.0 mg/kg.

3. The method of claim 1, wherein the dose is administered in a single aliquot.

4. The method of claim 1, wherein the dose is administered in two or more aliquots.

5. A method of treating anxiety in a patient comprising administering an effective non-toxic dose of wogonin to the patient.

6. A method of treating anxiety in a patient in need thereof comprising administering to the patient from about 0.1 mg/kg to about 10.35 mg/kg of a compound of the formula:

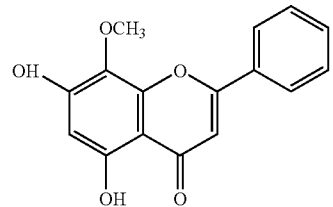

7. The method of claim 6, wherein the compound administered to the patient is from about 0.8 mg/kg to about 3.3 mg/kg.

8. A method of treating anxiety in a patient comprising administering a dose from about 0.1 mg/kg to about 10.35 mg/kg of wogonin to the patient.

* * * * *